(12) United States Patent
Palm (10) Patent No.: US 9,664,602 B2
(45) Date of Patent: May 30, 2017

(54) FILTERING DEVICE (75) Inventor: Thomas Palm, Jonstorp (SE)

(73) Assignee: FOSS ANALYTICAL AB, Hilleroed (DK)

( * ) Notice: Subject to any disclaimer, the term of this patent is extended or adjusted under 35 U.S.C. 154(b) by 1139 days.

(21) Appl. No.: 13/505,671

(22) PCT Filed: Dec. 9, 2009

(86) PCT No.: PCT/EP2009/066701
§ 371 (c)(1),
(2), (4) Date: May 2, 2012

(87) PCT Pub. No.: WO2011/069540
PCT Pub. Date: Jun. 16, 2011

(65) Prior Publication Data
US 2012/0225490 A1  Sep. 6, 2012

(51) Int. Cl.
| G01N 1/00 | (2006.01) |
| G01N 1/40 | (2006.01) |
| B01D 35/30 | (2006.01) |
| B01D 35/14 | (2006.01) |
| B65D 55/06 | (2006.01) |
| B65D 55/02 | (2006.01) |
| B01L 3/00 | (2006.01) |

(52) U.S. Cl.
CPC .............. *G01N 1/405* (2013.01); *B01D 35/14* (2013.01); *B01D 35/30* (2013.01); *B01L 3/56* (2013.01); *B65D 55/022* (2013.01); *B65D 55/06* (2013.01); *Y10T 436/25375* (2015.01)

(58) Field of Classification Search
CPC .... G01N 1/405; Y10T 436/25375; B01L 3/56

USPC ......................................................... 436/177
See application file for complete search history.

(56) References Cited

U.S. PATENT DOCUMENTS

| 5,133,470 | A | | 7/1992 | Abrams et al. |
| 5,254,242 | A | * | 10/1993 | van der Meer et al. ........ 210/91 |
| 5,269,030 | A | * | 12/1993 | Pahno et al. ...................... 5/604 |
| 6,184,039 | B1 | | 2/2001 | Komarek et al. |
| 6,479,295 | B1 | | 11/2002 | Komarek et al. |
| 6,877,631 | B1 | | 4/2005 | Thompson et al. |
| 7,510,686 | B2 | | 3/2009 | Schluter |
| 2003/0046914 | A1 | | 3/2003 | Zia et al. |
| 2003/0175166 | A1 | | 9/2003 | Schluter |
| 2005/0101021 | A1 | | 5/2005 | Kitcherside et al. |

(Continued)

FOREIGN PATENT DOCUMENTS

| EP | 1052508 A2 | 11/2000 |
| GB | 2252514 A | 8/1992 |
| WO | WO-9902959 A1 | 1/1999 |

(Continued)

*Primary Examiner* — Christopher A Hixson
*Assistant Examiner* — Emily Berkeley
(74) *Attorney, Agent, or Firm* — Harness, Dickey & Pierce, PLC (57) ABSTRACT

A single use filtering device comprises a filter body formed at least in part of a filter medium configured to hold a sample during filtration and a fastening element configured for releasably mounting the filtering device to a holder. The fastening element being adapted to undergo an irreversible structural alteration during the mounting or removal of the filtering device from the holder to prevent remounting of the filtering device to the holder.

11 Claims, 4 Drawing Sheets

(56) References Cited

U.S. PATENT DOCUMENTS

2005/0103702 A1\* 5/2005 Zia .................. B01D 35/30
                                                    210/435
2008/0217337 A1\* 9/2008 Rault ................. B65D 43/165
                                                    220/266

FOREIGN PATENT DOCUMENTS

| WO | WO-0066451  A1 | 11/2000 |
| WO | WO-0233403  A2 | 4/2002  |
| WO | WO-03006138 A1 | 1/2003  |

\* cited by examiner

FILTERING DEVICE

The present invention relates to a filtering device, particularly a one for use in the wet chemistry analysis of a sample and most particularly to a filtering device for use in the analysis of a foodstuff sample by fat extraction.

Wet chemistry analysis in the present context means an analysis of a sample involving the removal of one or more components of the sample by liquid chemical extraction and the subsequent analysis of one or both the residue and the extract by means of any of a number of known analysis techniques, including but not limited to, optical analysis techniques.

Wet chemistry analysis of foodstuff samples is important in quantifying the contents and nutritious values of food or fodder, such as the content of fat or fibre. During analysis of the fat content in food for example, the fat may be extracted from the food by solvent extraction. During the extraction, the food may be contained in a filtering device comprising a filter body for retaining a sample and which is formed, at least in part, by a filter medium.

The American patent with number U.S. Pat. No. 6,479,295 discloses a method for wet chemical analysis of samples for fat content by which a sample is contained in and encapsulated by a filter body formed entirely of a filter media. The patent application with number WO 02/33403 also discloses a filter container for use in the wet chemical analysis of the fat content of an item. Here, the filter container here comprises an impervious glass cylinder and a porous filter located at one end of the cylinder and being slidable therein. The patent application with number WO 99/02959 discloses a filter body formed of a filter medium retained in a rigid skeleton and suitable for the filtration of a food sample during fibre analysis.

It is a problem associated with the known filtering devices that after the wet chemical analysis residue may remain within the filter medium even if thoroughly cleaned. If the filtering device is then re-used the accuracy, the repeatability and/or the reproducibility of the analysis is likely to be adversely effected by the residue.

It is an object of the present invention to provide an improved filtering device for use in the wet chemical analysis of a contained sample.

According to a first aspect of the invention there is provided a single use filtering device comprising a filter body formed at least in part of a filter medium and configured to hold a sample during filtration and a fastening element adapted to retain the filter body, the fastening element being configured for releasably mounting the filter body to a holder, wherein the fastening element is adapted to undergo an irreversible structural alteration during the mounting or removal of the filtering device from the holder to inhibit the releasable remounting of the filtering device to the holder.

A single use filtering device is beneficial, as it eliminates the risk of contaminants remaining in the filtering device from previous samples. Thus, the single use filtering device according to the present invention may improve the accuracy, the repeatability and/or the reproducibility of wet chemical analysis, compared to multiple-use filtering devices.

The fastening element enables efficient mounting of the filtering device to a holder, which holder may be integral with or separate from an apparatus used in the wet chemical analysis process and which holder preferably has a complementary detent for engaging with the fastening element. The fastening element further enables efficient positioning of the filter body. Releasably mounting of the filtering device to a holder may be an effective way of holding the filter body in a desired position in relation to an apparatus or instrument.

The fastening element being arranged such that it is irreversibly structurally altered during mounting or removal of the filtering device from the holder to prevent remounting of the filtering device to the holder tends to ensure the single use of the filtering device, as a second use of the filtering device is inhibited, even prevented. Thus, problems associated with contaminants carried over from previous extractions may be minimised. As a result poor accuracy, repeatability and/or reproducibility which may be associated with the extraction are minimised.

The fastening element may be arranged for snap-fit mounting of said filtering device to said holder. Said snap-fit mounting may be an efficient way of mounting said filtering device to said holder. Said snap-fit mounting may further be an efficient way of arranging the fastening element for irreversible structural altering during mounting or removal to prevent remounting of the filtering device to the holder.

The fastening element may comprise at least one recess and/or at least one hole and/or at least one protruding member arranged to engage with said holder for said snap-fit mounting.

Said at least one recess and/or at least one hole and/or at least one member may be resilient. Said at least one recess and/or at least one hole and/or at least one member being resilient may enable efficient snap-fit mounting of said filtering device to said holder.

According to another aspect of the invention, there is provided a method for extraction of fat from a sample utilizing the filtering device according to the first aspect of the invention, comprising charging a filter body of a filtering device with the sample; mounting the filtering device to a holder by means of a fastening element of said filtering device; extracting fat from the sample contained in the filtering device; removing the filtering device from the holder, wherein the mounting or removing of said filtering device is performed such that the fastening element is irreversibly structurally altered to prevent remounting of the filtering device to the holder.

Mounting the filtering device to a holder by means of a fastening device may be efficient for mounting the filtering device to an apparatus.

Extracting fat from the sample in the filtering device may be efficient for separating the fat from other compounds of the sample, such as from the sample matrix. The fat may be extracted from the sample and out of the filtering device while other compounds of the sample may be retained in the filtering device. Extraction of fat from the sample may be employed as a step in an analysis of the fat in the sample.

Said irreversible structural altering of the fastening element is an effective means for preventing the filtering device from being remounted to the holder and thus re-use of the filtering device may be prevented.

Said fat extraction may further comprise hydrolysing the sample in the filtering device. Hydrolysing the sample in the filtering device may enable hydrolysis of the fat in the sample. Hydrolysis of the sample may release fat from the sample and make fat from the sample available for further treatment or analysis, such as extracting fat. Hydrolysis of the fat in the sample may make available free fatty acids, and thus free fatty acids originating from the sample may efficiently be, for example, extracted.

Said extracting fat may be preceded by said hydrolysing of the sample. Hydrolysis of the sample prior to extraction may free fat from the sample, for example in the form of free fatty acids, which may be extracted thereafter.

Said hydrolysis of the sample may take place in a first apparatus and said extracting fat may take place in a second apparatus. Said hydrolysis of the sample and said extracting fat taking place in a first and in a second apparatus respectively may enable efficient handling of both said hydrolysis of sample and said extracting of fat.

Said holder may be a part of said first apparatus. Said holder being a part of said first apparatus effectively prevents the first apparatus to be used a second time with the same filtering device.

Relevant parts of the explanations given above concerning the single use filtering device are also applicable to the method for extraction of fat from a sample. Reference is hereby made to these explanations.

The invention will now be explained in more detail, and specific embodiments, and variations of these, will be shown. The explanations are intended for illustrative and explanatory purposes and are not to be seen in any way as limiting to the scope of the invention. The illustrations are schematic and all details may not be illustrated, and all illustrated details may not be necessary for the invention.

The fat, as used herein, may refer to lipids. The fat may, for example, comprise fatty acids, free fatty acids, or tri-esters of glycerol and/or fatty acids.

The sample may contain fat. Hydrolysis of the fat in the sample may make available free fatty acids and/or fat chemically released from the sample, thus extraction of fat and/or free fatty acids originating from the sample may efficiently be enabled.

The hydrolysis may comprise hydrolysis of esters of fatty acids and glycerol.

The fatty acids or free fatty acids may be saturated or unsaturated.

The fat may be liquid or solid at room temperature, or a mixture of at room temperature liquid and solid fats.

The fat may be vegetable fat or animal fat, or mixtures thereof.

The fat may be fat present in the sample, naturally or as additives, or combinations thereof.

The fat may or may not be chemically bound to the sample, compounds of the sample, and/or the sample matrix. One fraction of the fat may be chemically bound to the sample, compounds of the sample, and/or the sample matrix, while another part may not be chemically bound to the sample, compounds of the sample, and/or the sample matrix.

Chemical bonds between the fat and the sample, compounds of the sample, and/or the sample matrix may be broken by said hydrolysing of the sample. Thus, said hydrolysing the sample in the filtering device may enable hydrolysis of fat bound to the sample and extracting the fat.

The breaking of chemical bonds may release fat bound to the sample, compounds of the sample, and/or the sample matrix, thus enabling efficient extracting of such fat from the sample.

The hydrolysis may break bonds within the fat, and bonds may be broken such that the fat releases, for example, free fatty acids, thus enabling efficient extracting of, for example, free fatty acids originating from the fat.

The sample may be, for example, food, foodstuffs, fodder or feed, or combinations thereof.

The filter medium of the filtering device may have pores adapted for retaining the sample or sample matrix but allowing fat to pass through. The release of the fat may be dependent of the polarity of the fluid which the filter medium is in contact with. If the filter medium is in contact with a solution in which the fat has poor solubility, such as an aqueous solution, the fat may remain in the filter body. If the filter medium is in contact with a solution in which the fat has high solubility, such as a solvent, for example an organic solvent, the fat may be released from the filter body through the filter medium.

The extraction may be realised by a flow of solvent passing the sample. The extraction may be realised by reflux of solvent, by heating the solvent such that solvent evaporates followed by condensation of the evaporated solvent and allowing the condensed solvent to pass the sample resulting in extracting fat possibly remaining in the sample.

The solvent may be an organic solvent, such as alcohol, ether, carbohydrate, or mixtures thereof, or aqueous solutions of any one of the solvents or aqueous solutions of any mixtures of the solvents.

The extracting fat from a sample may comprise hydrolysing the sample, extracting fat, or combinations thereof.

The filtering device may be removed from the holder after hydrolysing the sample; after extracting fat; after hydrolysing the sample and prior to extracting fat; after extracting fat and prior to hydrolysing the sample; or any suitable combination thereof.

The fastening element may be made of any suitable material, which material efficiently may be irreversibly structurally altered.

The fastening element may be from materials selected from the group consisting of polymers, such as plastics or rubbers; metals, such as iron, tin, steel, stainless steel, copper, or alloys; or combinations thereof, or any other suitable material or combinations of materials suitable for the purpose of the invention.

The filter body and/or the fastening element may be produced by moulding.

The holder may be a part of said first apparatus. The holder may additionally or alternatively be a part of said second apparatus. The holder may additionally or alternatively be an item separate from either apparatus.

The fastening element, may be arranged for any type of mounting of said filtering device to said holder. The fastening element may, for example, be arranged for snap-fit mounting, mounting by threading, or mounting as a result of friction between the fastening element and the holder, or combinations thereof.

The fastening element may comprise at least one recess and/or at least one hole and/or at least one protruding member arranged to engage with said holder for mounting of the filtering device to the holder.

The fastening element may comprise at least one recess and/or at least one hole and/or at least one protruding member arranged to engage with said holder for said snap-fit mounting.

Said at least one recess and/or at least one hole of the fastening element may engage with at least one protruding member of the holder, when the fastening element is mounted or being mounted to the holder.

Said at least one protruding member of the fastening element may engage with at least one recess and/or at least one hole of the holder, when the fastening element is mounted or being mounted to the holder.

Thus, the fastening element may engage with said holder by at least one recess and/or at least one hole receiving at least one protruding member of the holder and/or at least one protruding member being received by at least one recess and/or at least one hole of the holder.

Said at least one recess and/or at least one hole and/or at least one protruding member may be resilient Said at least one recess and/or at least one hole and/or at least one protruding member may be resilient for enabling efficient snap-fit mounting of said filtering device to said holder.

The filtering device may comprise at least one guide arranged to contact at least one feed-track of the holder, and/or the filtering device may comprise at least one feed-track arranged to contact at least one guide of the holder.

Said at least one guide and/or at least one feed-track of the filtering device may be arranged in contact with the filter and/or the fastening element.

Such a contact between at least one feed-track and at least one guide may be an efficient means of positioning the filter and/or the fastening element in relation to the holder during mounting of said filtering device to said holder.

Said guide may be, for example, a pin.

Said at least one protruding member may be a lug, tap, tongue, tine or flange.

The holder may, for example, be a part of a hydrolysis apparatus or a part of an extraction apparatus. It is realised that the holder may be part of any other apparatus or device suitable for the invention. Thus, the holder may be a part of or mounted to an analytical apparatus, a hydrolysing apparatus, or an extraction apparatus, or combinations thereof. The holder may be a releasable part of any such apparatus. The holder may be free and independent from an apparatus.

The holder may be moved, with the filtering device mounted to the holder, for example, between different apparatuses. Such movement may be realised by the holder being mounted to a robot or manually. The filtering device may be moved between said first and said second apparatus mounted to the holder. Said hydrolysing of the sample and said extracting fat may take place in a single apparatus.

Said irreversibly structurally altering may be, for example, plastic deformation, shape changing, tearing, splitting or tearing apart, destroying, cracking, or combinations thereof.

Any type of irreversible structurally altering of the fastening element during mounting or removal, to prevent remounting of the filtering device to the holder or re-use of the filter, may be used.

The irreversible structural altering may be the result of force, or chemical reactions or alterations involving the material of which the fastening element is made.

The fastening element may comprise weakenings of the material, such as a notch or relative thickness change, for achieving said irreversible structural altering.

Said irreversible structural altering of the fastening element may be an efficient means for preventing the filtering device from being remounted to the holder and thus re-use of the filtering device may be prevented.

Said fastening element may be arranged such that it is irreversibly structurally altered during the removal of the filtering device from the holder to prevent remounting of the filtering device to the holder Said fastening element may be arranged such that it is irreversibly structurally altered during the mounting of the filtering device from the holder to prevent remounting of the filtering device to the holder.

Said extracting fat from the sample in the filtering device may be efficient for separating the fat from other compounds of the sample. The fat may be extracted from the sample and out of the filtering device while other compounds of the sample are retained in the filtering device. Extraction of fat from the sample may be efficient for analysis of the fat in the sample.

Figure 1:
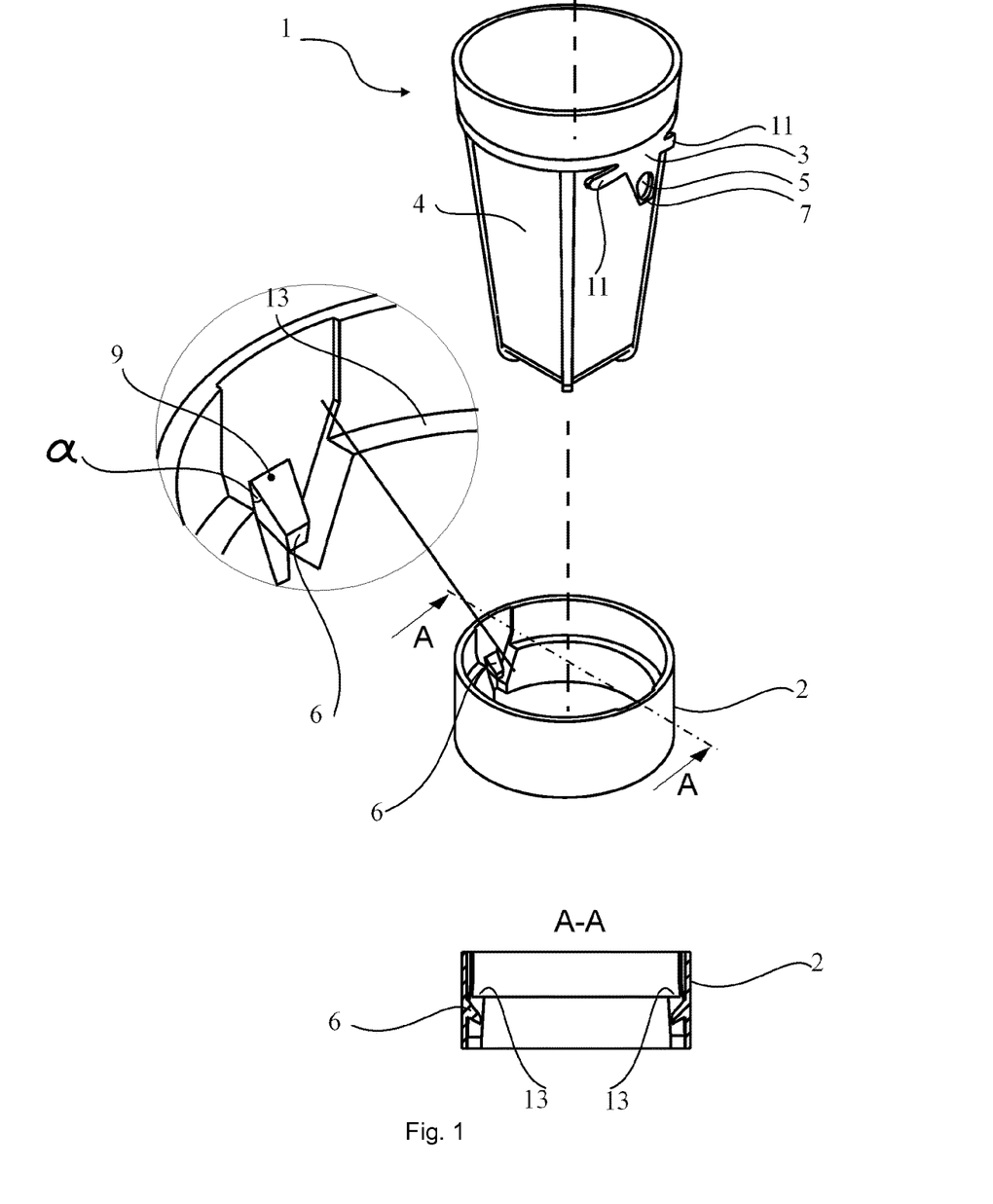
FIG. 1 illustrates a perspective view of a filtering device according to one embodiment of the invention and a holder, which filtering device has not been mounted to the holder.
Figure 2:
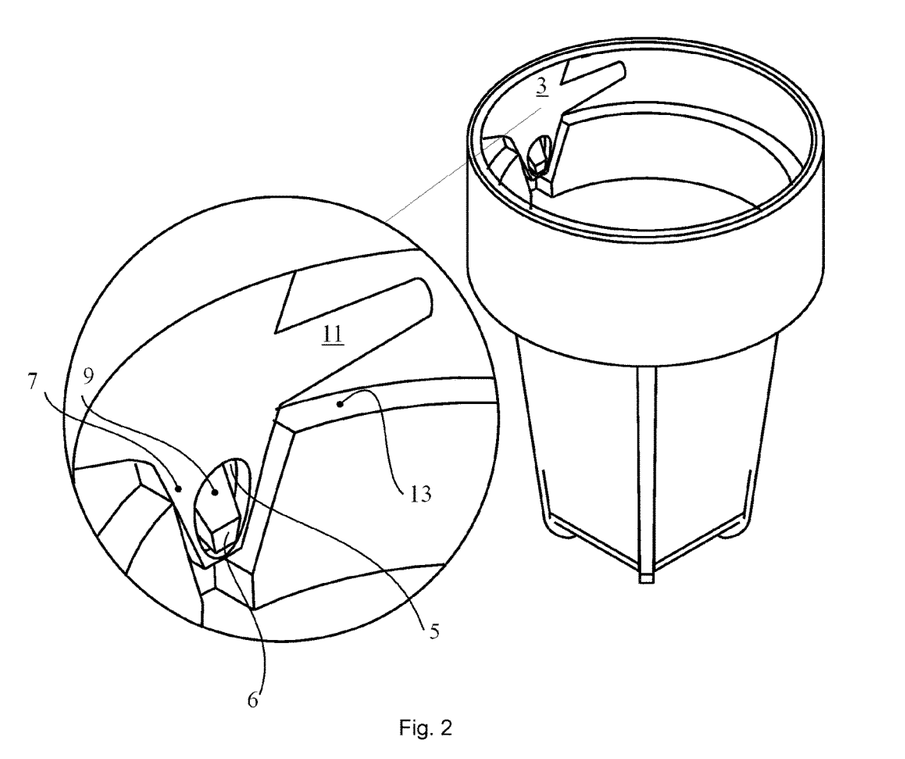
FIG. 2 illustrates a perspective view of a filtering device according to one embodiment of the invention and a holder, which filtering device is mounted to the holder.
Figure 3:
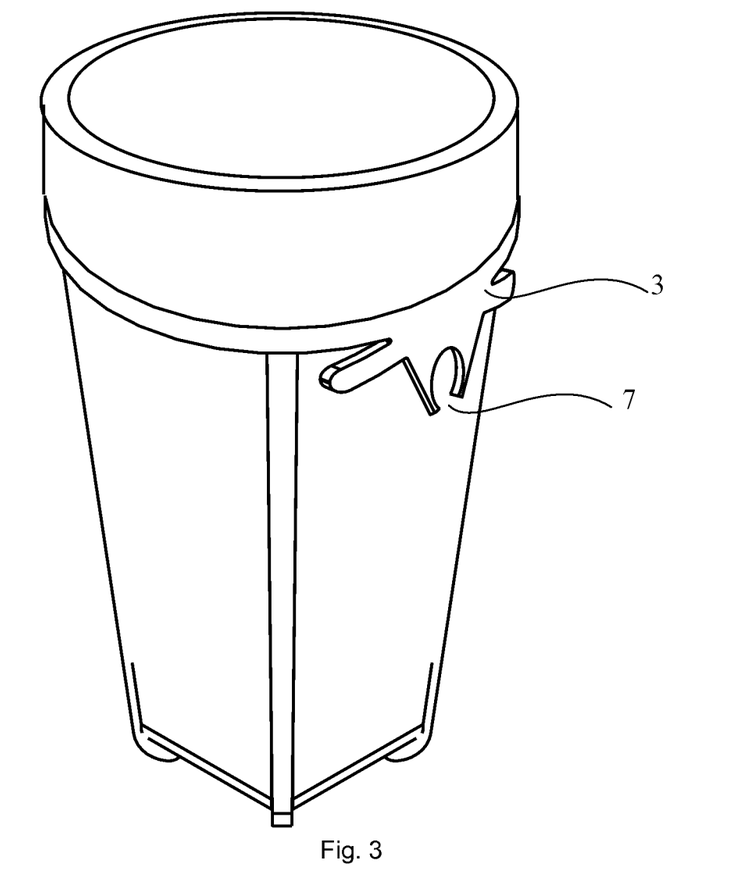
FIG. 3 illustrates a perspective view of a filtering device according to one embodiment of the invention and a holder, which filtering device has been removed from the holder.

With reference to FIGS. 1, 2, and 3 the mounting of a filtering device 1 to a holder 2, by snap-fit, and irreversible and structural altering of a fastening element 3 during removal of the filtering device 1 from the holder 2 are discussed. The filtering device 1 comprises the fastening element 3 and a filter body 4 which, in the present embodiment consists substantially entirely of a suitable filter medium.

FIG. 1 illustrates an exemplary embodiment of a filtering device 1 according to the present invention which has not yet been mounted to the holder 2. The fastening element 3, according to this embodiment, comprises a pair of generally identical and opposing through holes 5, each being a hole through the material of the fastening element 3. In this example, the filter body 4 is fastened to the fastening element 3 such that the holes 5 and the material 7 surrounding the holes 5 are positioned outside of the filter body 4 as seen in the illustration. The holder 2 comprises a pair of generally identical and opposing detents in the form of protruding members 6, each of which protrudes from the inner surface of the holder 2 with an upper surface 9 at an angle indicated by $\alpha$. The illustration in FIG. 1 is schematic, and the angle indicated by $\alpha$ may be larger or smaller than what is illustrated in the figure. According to this embodiment the fastening element 3 is made of flexible plastic, and as a result the material 7 surrounding the holes 5 is resilient and can be elastically deformed if a force or pressure is applied to it, such as a force from the protruding members 6 when the filtering device is being mounted to the holder 2. It is realised that there may be more or less than two holes 5 and corresponding protruding members 6, such as 1, 3, 4, 5, or more holes or protruding members.

With reference to FIGS. 2 and 3 only one of the holes 5 and a corresponding one of the protrusions 6 are illustrated and referred to. It will however be understood that any reference to the one hole 5 and protrusion 6 is intended to apply equally to the other hole and protrusion which are not illustrated.

FIG. 2 illustrates the filtering device 1 mounted to the holder 2 by inserting the filtering device 1 into the holder 2 in a direction from above. As the filtering device 1 is inserted into the holder 2, the resilient material 7 surrounding the hole 5 is bent in a direction toward the centre of the filtering device 1 as a result of pressure from the corresponding protruding member 6 as the material 7 contacts with and slides over the inclined surface 9, until it slides past the surface 9 and the material 7, being resilient causes the hole 5 to snap over the corresponding protruding member 6. In this manner the filtering device 1 is snap-fit mounted to the holder 2.

Alternatively, the material of the fastening element 3 may be relatively rigid plastic so that as a result the material 7 surrounding the hole 5 tends to resist deformation if a pressure is applied to it, such as from the protruding member 6. In this alternative embodiment the protruding member 6 is made elastically deformable such that it tends to move towards the inner surface of the holder 2 upon exertion of a suitable force, such as from the material 7 surrounding the hole 5 as the filtering device is inserted into the holder 2.

In the present embodiment and provided as an option only, the fastening element 3 further comprises a biasing means, here in the form of wings or tabs 11 which are formed of the resiliently flexible material 7. The biasing means 11 is intended for contact with a shoulder or protrusion, here illustrated as a ridge 13, located in the inner surface of the holder 2 before the holder 2 and filtering device 3 are snap-fit connected. As the biasing means 11 contacts the shoulder 13 it exerts a bias force tending to bias the filtering device 1 in a direction out of the holder 2. This bias force increases as the filtering device 1 is moved to achieve the snap-fit connection.

As can be seen in FIG. 2, the wings 11 are deformed upwards, in a direction opposite the direction of insertion of the filtering device 1 in the holder 2, as a result of the contact with the ridge 13 of the holder 2. Being formed of a resiliently flexible material 7 the wings 13 tend to resist this deformation and thus exert a bias force urging the base of the hole 5 into contact with the protrusion 6 and the filtering device 1 out of the holder 2. Thus the filtering device is advantageously held firmly in the holder 2 by a positive engagement of protrusion 6 with the material surrounding the hole 5.

As a result of the upper surface 9 of the detent 6, protruding at the angle indicated by the $\alpha$, the protruding member 6 acts as a barb if the filtering device 1 should be removed or attempted to be removed from the holder 2. As a result, the filtering device effectively cannot be removed from the holder 2 without the fastening element 3 being irreversibly structurally altered.

The hole 5 may be positioned at any other position of the fastening element 3. It is realised that the hole 5 could have been part of the holder, in which case the protruding member 6 would have been part of the fastening element 3.

In FIG. 3, the filtering device 1 has been removed from the holder 2, and the fastening element has been irreversibly structurally altered by the material 7 surrounding the hole 5 having been broken by the corresponding protruding member 6. In the present embodiment this is realised by arranging for a section of the material 7, here towards the base of the hole 5, being made thinner than other parts of the fastening element 3 surrounding the hole 5. It is realised that the irreversible structural altering may be realised in several other ways, for example, by a tab comprising a hole, which tab has weakenings, for example as provided by perforations, such that the tab would be torn off from the fastening element 3. As a result of the fastening element 3 being altered the filtering device 1 can no longer be fastened to the holder 2 properly a second time. Although, in this example, the filtering device 1 could be inserted a second time into the holder 2, the filtering device 1 would not be snap-fit mounted to the holder 2 and the filtering device 1 would not be secured to the holder 2. In the present embodiment the wings 11 now also help prevent the filtering device 1 being reliably held in the holder 2 a second time since the fastening element 3 can no longer engage with the detent 6 to resist the bias force that is exerted by the wings 11 as they are urged against the ridge 13 during mounting.

As a result the filtering device 1 would not function properly during re-use, as it would not be held safely in position in relation to the holder 2, and it might, for example, float or sink out of position, if positioned in a liquid, such as during hydrolysis of the sample or during extraction of fat from the sample. Thus, the fastening element 3 of the filtering device 1 is an effective means for ensuring the single use of a filter medium of the filter body 4, as a second use of the filtering device 1 is prevented. Thus, problems associated with contaminants from previous samples left in contact with the filter medium or remaining contained within the filter body 4.

Figure 4:
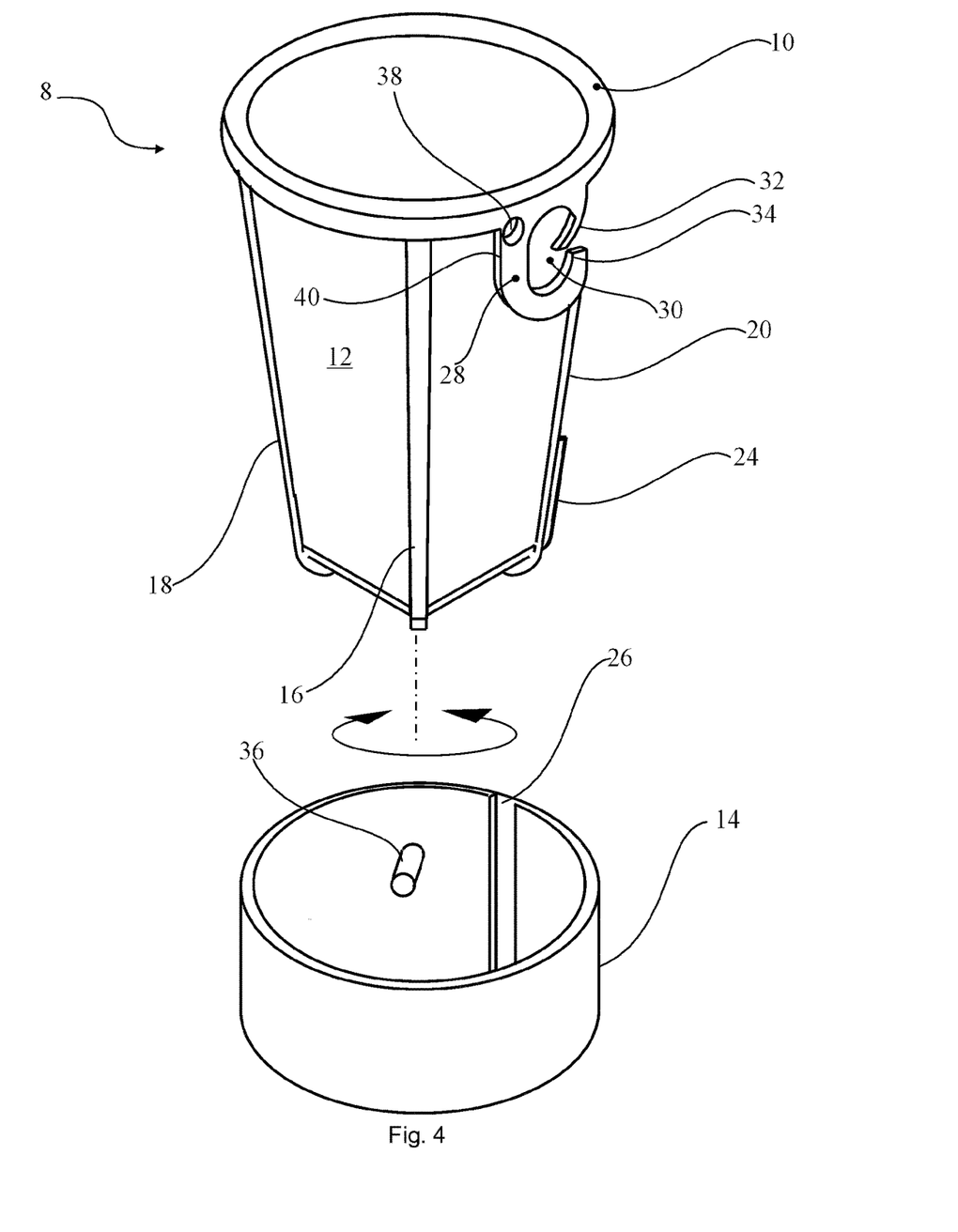
FIG. 4 illustrates a perspective view of a filtering device according to a second embodiment of the invention, which filtering device has not yet been mounted to the illustrated holder.

In FIG. 4 a filtering device 8 according to a further embodiment of the present invention is shown comprising a fastening element 10 and filter body 12. The filtering device 8 is illustrated as not yet being mounted in holder 14.

The fastening element 10 is, in the present example, provided with support legs 16, 18, 20 (although greater or fewer may be provided) by which is supported the filter body 12.

A tongue 24 is here provided on a support leg 20 which is intended to engage with and slide in a corresponding groove 26 in the holder 14 to limit the relative orientation of the filtering device 8 and holder 14 as it is inserted into the holder 14 from above. The length of the tongue 24 is selected so that it engages with the groove 26 as the filtering device 8 is entered into the holder 14 to initially prevent rotation of the filtering device 8 in the holder 14 but slides free of the groove 26 as the filtering device 8 is fully inserted into the holder 14. In this manner the filtering device 8 may be rotated in the holder 14 when fully mounted.

In the present embodiment the fastening element 10 is provided with a snap-hook 28 in which is formed a hole 30 closed by a flexible tine 32 connected at one end so as to be able to move in to the hole 30 when urged in that direction by an external force. Upon removal of the external force the tine 32 is self-biased to move back towards its position closing the hole 30. Movement of the tine 32 in the opposite direction, away from the hole is prevented by its engagement with a lip 34 of the snap-hook 28.

The snap-hook 28 of the fastening element 10 is designed to undergo an irreversible structural alteration in response to the exertion of a force upon it.

The holder 14 is provided with a pin 36 which extends inwards from an inner surface of the holder 14 and which engages with the snap-hook 28 when the filtering device 8 and holder 10 are rotated relative to one another around a longitudinal axis of the filtering device 8 after the filtering device 8 is fully received in the holder 14. Relative rotation in one direction will bring the pin 36 into contact with a rear surface 40 of the snap-hook 28 and prevent engagement of the pin 36 with the snap-hook 28. Relative rotation in the other direction will bring the pin 36 into contact with the flexible tine 32 of the snap-hook 28. Further rotation in this direction will cause the tine 32 to move inwards and allow the pin 36 to enter the hole 30 of the snap-hook 28 after which the tine 32 will tend to return to its initial position closing the hole 30 and fastening the filtering device 8 in the holder 14. Continued rotation in this direction, typically when removing the filtering device 8, will urge the pin against the snap-hook 28 so as to exert a force of on the snap-hook 28 in a direction away from the hinged tine 32 and so cause a failure of the snap-hook at the weakening 38.

As a result of the fastening element 10 being irreversibly altered in this manner the filtering device 8 can no longer be fastened to the holder 14 properly a second time.

In the present embodiment the snap-hook 28 is provided with a structural weakness (here a thinning of the material of the fastening element 10) at a location 38 where the snap-hook 28 connects to the main body of the fastening element 10 and generally opposite the flexible tine 32. However, in an alternative embodiment, the tine 32 may be provided with a structural weakness. If the filtering device 8 is rotated to urge the pin 36 back into contact with the tine 32 after the pin 36 has been located in the hole 30, typically when removing the filtering device, the fastening element 10 will be irreversibly structurally altered by structural failure of the tine 32.

Whilst the invention has been exemplified above by a fastening element in which the irreversible structural alteration requires a physical interaction between elements of the filtering device and those of a holder it will be appreciated that the irreversible structural alteration of the fastening element may be achieved in other ways without departing from the invention as claimed. For example a portion of the fastening element may be formed of a different material selected to react, for example dissolve, after contact with chemicals employed in a filtration process in which the filtering device is intended for use so as to achieve the necessary irreversible structural alteration.

An exemplary method for extraction of fat from a sample employing a single use filtering device according to the present invention will now be discussed as an illustration of the usefulness of the filtering device 1 in wet chemical analysis procedures.

A sample, in this example food, is weighed and charged in a filter of a filtering device. The filtering device with sample is mounted to a holder of a hydrolysis apparatus, by means of the fastening element of the filtering device. The hydrolysis apparatus comprises a container with a warm aqueous solution of hydrochloric acid (HCl), and the filtering device mounted to the holder is positioned such that the filter with the sample is submerged in the solution wherein hydrolysis occurs, allowing HCl to pass through the filter and react with the sample, while the holder remains above the HCl surface. The hydrolysis results in breaking of chemical bonds, resulting in freeing of fat bound to the sample matrix. Due to the solution being aqueous and the fat being poorly or not at all soluble in aqueous solution, the fat remains in the filtering device in proximity to or in contact with the sample.

After hydrolysis, the solution is removed and the filter with the sample and free fat is rinsed in water followed by drying. The filtering device is removed from the holder resulting in the fastening element being irreversibly structurally altered, such that the filtering device cannot be mounted a second time to the holder.

Afterwards, the filtering device, with the sample and free fat, is positioned in an extraction apparatus for extracting fat from the sample. During said extracting fat, the sample and fat in the filter is submerged in solvent with such properties that the fat has high solubility in the solvent, which solvent passes through the filter, and as one result the fat is extracted from the sample to the solvent and allowed to pass through the filter to the solvent outside of the filter. The solvent containing fat may thereafter be treated, for example by heating or/and reducing the pressure, such that solvent is evaporated and dried fat remaining. The remaining fat may be weighed and thus the fat content of the sample may be estimated.

The extraction of fat may be conducted by heating the solvent in which the filter is submerged such that solvent will evaporate. The evaporated solvent may then be condensed and allowed to drip back into the filter in which fat may be extracted to the solvent and allowed to pass through the filter by the solvent after which the solvent may evaporate, be condensed and enter the filter again for extraction of fat.

The solvent may be organic solvent, and the solvent may be selected such that the fat has high or good solubility in the solvent.

As a result of the filtering device not being able to efficiently be remounted, or mounted a second time, to the holder, the risk of contaminants remaining in the filtering device from previous samples is eliminated. Thus, the single use filtering device may improve the accuracy, the repeatability and/or the reproducibility of the extraction as compared to multiple-use filtering devices.

The invention claimed is:

1. A single use filtering device configured to be releasably fastened to a filter holder, the filtering device being separate from the filter holder, the filtering device comprising:
   a filter body formed at least in part of a filter medium, the filter body being configured to hold a sample during filtration; and
   a fastener configured to retain the filter body, the fastener being configured to releasably fasten to the filter holder that is separate from the filtering device, such that the filtering device is secured to the filter holder,
   wherein the fastener is configured to undergo an irreversible structural alteration during fastening or removal of the filtering device from the filter holder to inhibit re-fastening of the filtering device to the filter holder,
   wherein the fastener is configured to snap-fit mount said filtering device to said filter holder,
   wherein the fastener comprises at least one selected from a group consisting of at least one recess, at least one hole and at least one protruding member arranged to engage with said filter holder for said snap-fit mounting,
   wherein the fastener includes a snap-hook.

2. The single use filtering device according to claim 1, wherein said at least one selected from the group consisting of at least one recess, at least one hole and at least one protruding member is formed in a resilient material.

3. Method for extraction of fat from a sample, comprising:
   charging the filter body of the filtering device according to claim 1 with the sample;
   fastening the filtering device to the filter holder using the fastener of said filtering device;
   extracting fat from the sample in the filtering device; and
   removing the filtering device from the filter holder,
   wherein the fastening or the removing of said filtering device causes the fastener to undergo the irreversible structural alteration to inhibit the re-fastening of the filtering device to the filter holder.

4. The method according to claim 3, further comprising: hydrolysing the sample in the filtering device.

5. The method according to claim 4, wherein said extracting fat is preceded by said hydrolysing of the sample in the filtering device.

6. The method according to claim 4, wherein said hydrolysis of the sample takes place in a first apparatus and said extracting fat takes place in a second apparatus.

7. The method according to claim 6, wherein said filter holder is a part of said first apparatus.

8. A filter arrangement, comprising:
   the filtering device according to claim 1; and
   the filter holder wherein the filter holder is adapted to releasably hold the filtering device and is provided with a detent which is adapted to engage the fastener when the filtering device is fastened and to cooperate there-with to effect the irreversible structural alteration of the fastener during the fastening or removal of the filtering device to inhibit the re-fastening of the filtering device to the filter holder.

9. A filter arrangement as claimed in claim 8, wherein the filtering device further includes a biasing member, and
the filter holder includes a shoulder configured to contact with the biasing member before the detent engages the fastener, the biasing member and the shoulder being configured to collectively exert a bias force to move the filtering device out of the filter holder.

10. A filter arrangement as claimed in claim 8, wherein the fastener includes a flexible tine connected at a first end, and a lip at a second end, the tine being moveable, the tine further being configured to exert a bias force against the lip to prevent movement of the tine beyond the lip.

11. A filtering assembly, comprising:
a filter holder that defines an interior space; and
a single use filtering device configured to be releasably fastened to the filter holder, the filtering device including,
a filter body formed at least in part of a filter medium, the filter body being configured to hold a sample during filtration, and
a fastener configured to retain the filter body, the fastener being configured to releasably fasten to the filter holder, such that the filtering device is secured to the filter holder and the filter body at least partially extends into the interior space of the filter holder,
wherein the fastener is configured to undergo an irreversible structural alteration during fastening or removal of the filtering device from the filter holder to inhibit re-fastening of the filtering device to the filter holder.

* * * * *